(12) United States Patent
Mayer

(10) Patent No.: US 6,664,243 B1
(45) Date of Patent: Dec. 16, 2003

(54) BENZYLLACTOBIONAMIDES AS INHIBITORS OF SMOOTH MUSCLE CELL PROLIFERATION

(75) Inventor: Scott C. Mayer, Robbinsville, NJ (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 09/444,736

(22) Filed: Nov. 22, 1999

Related U.S. Application Data

(60) Provisional application No. 60/126,442, filed on Nov. 24, 1998.

(51) Int. Cl.⁷ ................. A61K 31/715; C08B 37/00
(52) U.S. Cl. .................. 514/53; 514/23; 514/25; 514/42; 536/1.11; 536/4.1; 536/17.2; 536/17.9; 536/29.1; 536/53; 536/54; 536/116; 536/118; 536/123.13; 536/18.7
(58) Field of Search ................. 536/123.13, 1.11, 536/4.1, 17.2, 17.9, 29.1, 53, 54, 116, 118, 18.7; 514/23, 25, 42, 53

(56) References Cited

U.S. PATENT DOCUMENTS

| | | | |
|---|---|---|---|
| 2,752,334 A | 6/1956 | Walton | |
| 4,431,637 A | 2/1984 | Upeslacis et al. | 424/180 |
| 5,008,247 A | * 4/1991 | Meinetsberger | 536/123.13 |
| 5,019,562 A | 5/1991 | Folkman et al. | 514/58 |
| 5,037,973 A | 8/1991 | Meinetsberger | 536/53 |
| 5,296,588 A | 3/1994 | Au et al. | 536/1.11 |
| 5,310,542 A | 5/1994 | Au et al. | 424/52 |
| 5,336,765 A | 8/1994 | Au et al. | 536/18.5 |
| 5,464,827 A | 11/1995 | Soll | 514/58 |
| 5,498,775 A | 3/1996 | Novak et al. | 514/25 |
| 5,686,603 A | * 11/1997 | Au et al. | 536/123.13 |

FOREIGN PATENT DOCUMENTS

| | | | |
|---|---|---|---|
| EP | 0312086 | 4/1989 | C07H/15/04 |
| EP | 0312087 | 4/1989 | C07H/15/04 |
| EP | 0356275 | 2/1990 | C08B/37/10 |
| EP | 0454220 | 10/1991 | C07H/15/04 |
| EP | 0550106 | 7/1993 | C07H/15/04 |
| EP | 0551675 | 7/1993 | A61K/7/16 |
| WO | 9006755 | 6/1990 | A61K/31/70 |
| WO | 9309790 | 5/1993 | A61K/31/70 |
| WO | 9614324 | 5/1996 | C07H/15/203 |
| WO | 9614325 | 5/1996 | C07H/15/203 |

OTHER PUBLICATIONS

Bognar et al. "Derivatives of aldonic and aldaric acids" Ber. 1963, 96, 689–693.*
Bognar et al. "Preparations and reactions of D–glucaric acid derivatives" Magy. Kem. Folyoirat, 1963, 69 (10), 450–453.*
Bertho, A. Liebigs Ann. Chem. 1949, vol. 562, 229–239, with English translation supplied by Applicant.*
Klein, U. et al. Liebigs Ann. Chem. 1987, 485–489, with English translation supplied by Applicant.*
Kohji Ohno, Takeshi Fukuda, Hiromi Kitano, "Free Radical polymerization of a sugar residue–carrying styryl monomer with a lipophilic alkoxyamine initiator: synthesis of a well- –defined novel glycolipid", Macromol. Chem. Phys., 199, 2193–2197 (1998).
Zehavi, Carbohyd. Res., 1986, 151, 371.
Reilly et al., Drug Development Research, 1993, 29, 137.
Durette et al., Carbohydrate Research, 1978, 67, 484–490.
Kopper et al., Carbohydrate Research, 1989, 193, 296–302.
Zehavi et al., Carbohydrate Research, 1983, 124, 23–34.
Zehavi et al., Carbohydrate Research, 1992, 228, 255–263.
Connors et al., Herba Polonica, 1998, 44, 33–38.
Morales et al., Angew. Chem. Int. Ed., 1988, 37 (5), 654–657.

* cited by examiner

*Primary Examiner*—Kathleen K. Fonda
(74) *Attorney, Agent, or Firm*—Michael R. Nagy

(57) ABSTRACT

This invention provides smooth muscle cell proliferation inhibitors of formula I having the structure

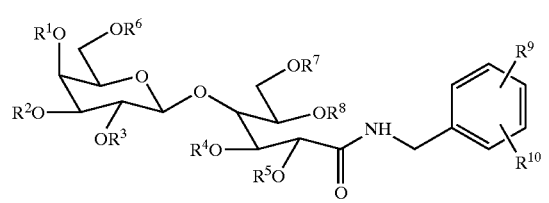

wherein $R^1$–$R^{13}$ are as defined herein.

5 Claims, No Drawings

BENZYLLACTOBIONAMIDES AS INHIBITORS OF SMOOTH MUSCLE CELL PROLIFERATION

This application claims the benefit of U.S. Provisional Application No. 60/126,442 filed on Nov. 24, 1998, now abandoned, which was converted from U.S. patent application Ser. No. 09/198,982, filed Nov. 24, 1998, pursuant to a petition filed under 37 C.F.R. 1.53(c)(2)(i).

BACKGROUND OF THE INVENTION

This invention relates to the use of substituted benzyllactobionamides as smooth muscle cell proliferation inhibitors and as therapeutic compositions for treating diseases and conditions which are characterized by excessive smooth muscle proliferation such as restenosis.

All forms of vascular reconstruction such as angioplasty and vein bypass procedures effect a response to injury that ultimately leads to smooth muscle cell (SMC) proliferation and subsequently, deposition of profuse amounts of extracellular matrix (Clowes, A. W.; Reidy, M. A. *J. Vasc. Surg* 1991, 13, 885). These events are also central processes in the pathogenesis of atherosclerosis (Raines E. W.; Ross R. *Br. Heart J.* 1993, 69 (Supplement), S. 30) as well as transplant arteriosclerosis (Isik, F. F.; McDonald, T. O.; Ferguson, M.; Yamanaka, E.; Gordon *Am. J. Pathol.* 1992, 141, 1139). In the case of restenosis following angioplasty, clinically relevant solutions for controlling SMC proliferation through pharmacological intervention have remained elusive to date (Herrman, J. P. R.; Hermans, W. R. M.; Vos, J.; Serruys P. W. *Drugs* 1993, 4, 18 and 249). Any successful approach to selective SMC proliferation inhibition must not interfere with endothelial cell repair or the normal proliferation and function of other cells (Weissberg, P. L.; Grainger, D. J.; Shanahan C. M.; Metcalfe, J. C. *Cardiovascular Res.* 1993, 27, 1191).

The glycosaminoglycans heparin and heparan sulfate are endogenous inhibitors of SMC proliferation, yet are able to promote endothelial cell growth (Castellot, J. J. Jr.; Wright, T. C.; Karnovsky, M. J. *Seminars in Thrombosis and Hemostasis* 1987, 13, 489). However, the full clinical benefits of heparin, heparin fragments, chemically modified heparin, low molecular weight heparins, and other heparin mimicking anionic polysaccharides may be compromised due to other pharmacological liabilities (excessive bleeding arising from anticoagulation effects, in particular) coupled with heterogeneity of the various preparations (Borman, S. *Chemical and Engineering News*, Jun. 28, 27, 1993).

U.S. Pat. Nos. 5,296,588, 5,336,765, and EP 550106A1 describe an improved process of preparing N-substituted aldonamides. U.S. Pat. No. 5,310,542 and EP 551675-A1 also describe glycosides (specifically aldobionamides) being used in oral hygiene compositions to act as antimicrobial agents and inhibit formation and/or growth of bacteria responsible for dental plaque. U.S. Pat. No. 2,752,334 describes a process of preparing N-substituted lactobionamides and their use as emulsifying agents (specially for cheese) and antimycotic agents. The compounds of the present invention differ in that the compounds of this invention (a) are acetylated or sulfated benzyllactobionamides, (b) have substituents on the aromatic core that are different, and (c) are being used as smooth muscle cell antiproliferatives.

EP 312086 A2 and EP 312087 A2 describe polysulfate ester(s) of bis-aldonic acid amide derivatives as antiinflammatory and antithrombotic agents. The compounds of the present invention differ in that the compounds (a) are being used as smooth muscle cell antiproliferatives, (b) are not dimeric in nature, and (c) contain no more than two contiguous sugar residues (disaccharide).

(Klein, U.; Mohrs, K.; Wild, H.; Steglich, W. *Liebigs Ann. Chem.* 1987, 485–489.) describes the use of peracetylated aldonamides to prepare 3-substituted pyrazoles. The compounds of the present invention differ in that the compounds (a) have substituents on the aromatic core that are different, (b) are not substituted at the benzylic position, (c) are being used as smooth muscle cell antiproliferatives, and (d) are not used as precursors to pyrazoles.

U.S. Pat. No. 5,498,775, WO 96/14324, and U.S. Pat. No. 5,464,827 describe polyanionic benzylglycosides or cylcodextrins as smooth muscle cell proliferation inhibitors for treating diseases and conditions that are characterized by excessive smooth muscle proliferation. β-Cyclodextrin tetradecasulfate has been described as a smooth muscle cell proliferation inhibitor and as an effective inhibitor of restenosis (Reilly, C. F.; Fujita, T.; McFall, R. C.; Stabilito, I. I.; Wai-si E.; Johnson, R. G. *Drug Development Research* 1993, 29, 137). U.S. Pat. No. 5,019,562 discloses anionic derivatives of cyclodextrins for treating pathological conditions associated with undesirable cell or tissue growth. WO 93/09790 discloses antiproliferative polyanionic derivatives of cyclodextrins bearing at least 2 anionic residues per carbohydrate residues. Meinetsberger (EP 312087 A2 and EP 312086 A2) describes the antithrombotic and anticoagulant properties of sulfated bis-aldonic acid amides. U.S. Pat. No. 4,431,637 discloses polysulfated phenolic glycosides as modulators of the complement system. The compounds of the present invention differ from all of the prior art in that the compounds (a) are benzyllactobionamides which bear no structural resemblance to heparin or sulfated cyclodextrins, (b) are compounds which are not dimeric in nature, (c) contain no more than two contiguous sugar residues (disaccharide), and (d) are of defined structure.

WO 9614325 discloses acylated benzylglycosides as smooth muscle cell proliferation inhibitors. The compounds of the present invention differ in that (a) the saccharide backbone is different, (b) the open chain core has preparation advantages over the cyclic array, and (c) the substituents on the carbohydrate backbone are different.

(Zehavi, U.; Herchman, M. *Carbohyd. Res.* 1986, 151, 371) discloses 4-carboxy-2-nitrobenzyl 4-O-α-D-glucopyranosyl-β-D-glucopyranoside which is attached to a polymer for study as an acceptor in the glycogen synthase reaction. The compounds of the present invention differ from those of the Zehavi disclosure in that (a) the substituents on the benzyl groups are different and (b) the use (smooth muscle antiproliferation) is different.

DESCRIPTION OF THE INVENTION

This invention provides benzyllactobionamides of formula I

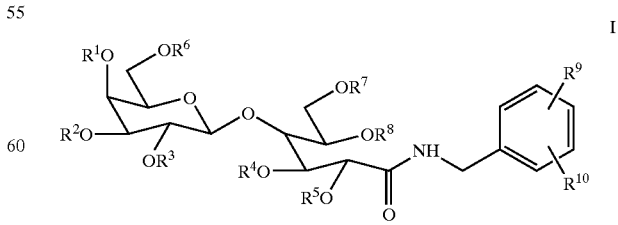

wherein
$R^1, R^2, R^3, R^4, R^5, R^6, R^7$, and $R^8$ are each, independently, acyl of 2–7 carbon atoms, haloacyl of 2–7 carbon atoms, nitroacyl of 2–7 carbon atoms, cyanoacyl of 2–7 carbon atoms, trifluoromethylacyl of 3–8 carbon atoms, benzoyl, or —SO$_3$H;

R$^9$ is hydrogen, CN, NO$_2$, halo, CF$_3$, alkyl of 1–6 carbon atoms, or alkoxy of 1–6 carbon atoms;

R$^{10}$ is hydrogen, —NO$_2$, —NHR$^{11}$, —NHR$^{13}$, —N(R$^{13}$)$_2$, —NCH$_3$R$^{13}$, —NHCO$_2$alkyl, wherein the alkyl moiety contains 1–6 carbon atoms, alkylsulfonamide of 1 to 4 carbon atoms,

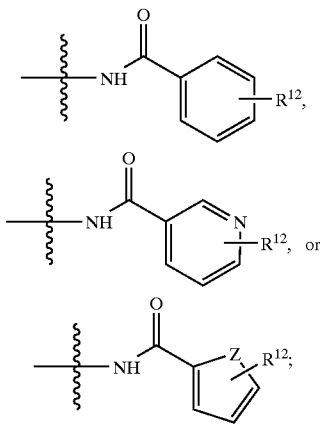

Z is O or S;

R$^{11}$ is an α-amino acid in which the α carboxyl group forms an amide with the nitrogen of R$^{10}$, wherein if said amino acid is glutamic acid or aspartic acid, the non-α carboxylic acid is an alkyl ester in which the alkyl moiety contains from 1–6 carbon atoms;

R$^{12}$ is hydrogen, CN, NO$_2$, halo, CF$_3$, alkyl of 1–6 carbon atoms, alkoxy of 1–6 carbon atoms, acyl of 2–7 carbon atoms, or benzoyl;

R$^{13}$ is hydrogen, acyl of 2–7 carbon atoms, haloacyl of 2–7 carbon atoms, nitroacyl of 2–7 carbon atoms, cyanoacyl of 2–7 carbon atoms, trifluoromethylacyl of 3–8 carbon atoms, or benzoyl;

or a pharmaceutically acceptable salt thereof.

Alkyl includes both straight chain as well as branched moieties. Halogen means bromine, chlorine, fluorine, and iodine. When R$^{11}$ is an α-amino acid, the carboxyl moiety exists as an amide with the amide nitrogen being bonded to the phenyl ring of the compound of formula I. The following exemplifies the resulting structure when R$^{11}$ is alanine:

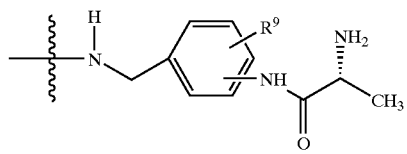

When the amino acid contains a second carboxyl moiety, the moiety is an alkyl ester of the free acid. The following example shows aspartic acid methyl ester.

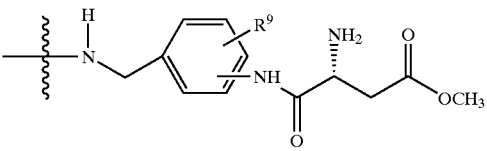

Preferred amino acids include alanine, arginine, aspartic acid, cystine, glutamic acid, glycine, histidine, isoleucine, leucine, lysine, methionine, phenylalanine, proline, serine, threonine, tryptophan, tyrosine, and valine. The amino acids defined by R$^{11}$ include both the D and L amino acids.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from organic and inorganic bases, preferably alkali metal salts, for example, sodium, lithium, or potassium. Acid addition salts can be prepared when a compound of this invention contains a basic nitrogen, and base addition salts can typically be prepared when the compound of formula I contains a —SO$_3$H moiety.

The compounds of this invention may contain an asymmetric carbon atom or sulfoxide moiety and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Preferred compounds of this invention are benzyllactobionamides of formula I

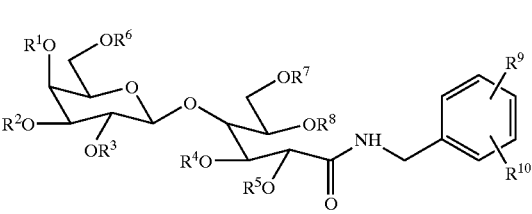

wherein

R$^1$, R$^2$, R$^3$, R$^4$, R$^5$, R$^6$, R$^7$, and R$^8$ are each, independently, acyl of 2–7 carbon atoms or —SO$_3$H;

R$^9$ is hydrogen, CN, NO$_2$, halo, CF$_3$, alkyl of 1–6 carbon atoms, or alkoxy of 1–6 carbon atoms;

R$^{10}$ is hydrogen, —NO$_2$, NHR$^{11}$, —NHR$^{13}$, —N(R$^{13}$)$_2$, —NCH$_3$R$^{13}$, —NHCO$_2$alkyl, wherein the alkyl moiety contains 1–6 carbon atoms, alkylsulfonamide of 1 to 4 carbon atoms,

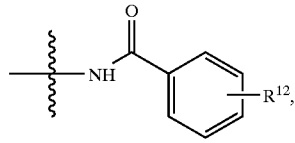

-continued

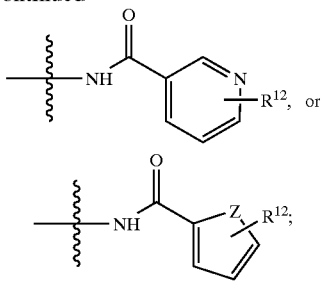

Z is O;

R[11] is an α-amino acid in which the α carboxyl group forms an amide with the nitrogen of R[10], wherein if said amino acid is glutamic acid or aspartic acid, the non-α carboxylic acid is an alkyl ester in which the alkyl moiety contains from 1–6 carbon atoms;

R[12] is hydrogen, CN, NO$_2$, halo, CF$_3$, alkyl of 1–6 carbon atoms, alkoxy of 1–6 carbon atoms, acyl of 2–7 carbon atoms, or benzoyl;

R[13] is hydrogen, acyl of 2–7 carbon atoms, haloacyl of 2–7 carbon atoms, nitroacyl of 2–7 carbon atoms, cyanoacyl of 2–7 carbon atoms, trifluoromethylacyl of 3–8 carbon atoms, or benzoyl;

or a pharmaceutically acceptable salt thereof.

More preferred compounds of this invention are benzyl-lactobionamides of formula I

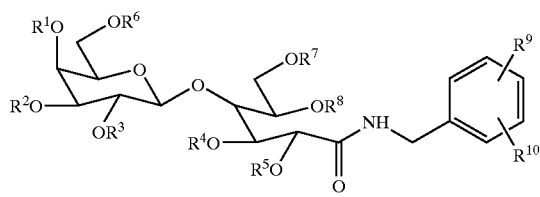

wherein

R[1], R[2], R[3], R[4], R[5], R[6], R[7], and R[8] are each, independently, acetyl or —SO$_3$H;

R[9] is hydrogen, CN, NO$_2$, halo, CF$_3$, alkyl of 1–6 carbon atoms, or alkoxy of 1–6 carbon atoms;

R[10] is hydrogen, —NO$_2$, —NHR[13], —N(R[13])$_2$,

R[13] is hydrogen, or acyl of 2—7 carbon atoms;

or a pharmaceutically acceptable salt thereof.

Specifically preferred compounds of this invention are:

N-Benzyl-octa-O-acetyl-lactobionamide or a pharmaceutically acceptable salt thereof;
N-Benzyl-octa-O-sulfo-lactobionamide or a pharmaceutically acceptable salt thereof;
N-(4-Nitro-benzyl)-octa-O-acetyl-lactobionamide or a pharmaceutically acceptable salt thereof;
N-(4-Amino-benzyl)-octa-O-acetyl-lactobionamide or a pharmaceutically acceptable salt thereof;
N-(3-Amino-benzyl)-octa-O-acetyl-lactobionamide or a pharmaceutically acceptable salt thereof;
N-[3-(Acetylamino)-benzyl]-octa-O-acetyl-lactobionamide or a pharmaceutically acceptable salt thereof; and
N-[3-(Acetylamino)-benzyl]-octa-O-sulfo-lactobionamide or a pharmaceutically acceptable salt thereof;

The compounds of this invention were prepared according to the following scheme from commercially available starting materials or starting materials which can be prepared using literature procedures. This scheme shows the preparation of representative compounds of this invention.

Lactobiono-1,5-lactone (1, *H. S. Isbell; H. L. Frush. Methods Carbohyd. Chem. 1963, 2, 16–18.) is coupled with a benzyl amine 2 (in the presence of sodium carbonate when using amine salt) in a protic solvent such as methanol at temperatures ranging from 0 to 60° C. to yield glycoside 3 (Scheme 1). Reduction of the nitro group of 3 can be accomplished with a reducing agent such as stannous chloride in a polar aprotic solvent such as ethyl acetate at ambient temperature to reflux to afford an anilino compound 4. Coupling of 4 with an acid chloride can be completed in the presence of an amine base such as triethylamine or diisopropylethylamine or using a stronger base such as sodium hydride (for sterically hindered systems) in an aprotic solvent such as dichloromethane or tetrahydrofuran at temperatures ranging from 0° C. to ambient temperature to yield the target compound 5. The peracetylated compound 5 can be converted to its octahydroxy intermediate with catalytic sodium methoxide in methanol or aqueous sodium hydroxide in methanol at temperatures ranging from ambient temperature to reflux. This intermediate can be further converted to the octasulfo compound 6 with sulfur trioxide trimethylamine complex in a polar solvent such as N,N-dimethylformamide at reflux. Many salts of the sulfate group can be prepared by using different ion exchange columns such as Dowex Na$^+$ or K$^+$.

Scheme 1

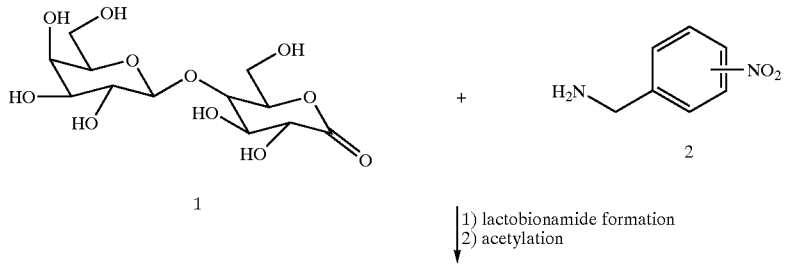

1) lactobionamide formation
2) acetylation

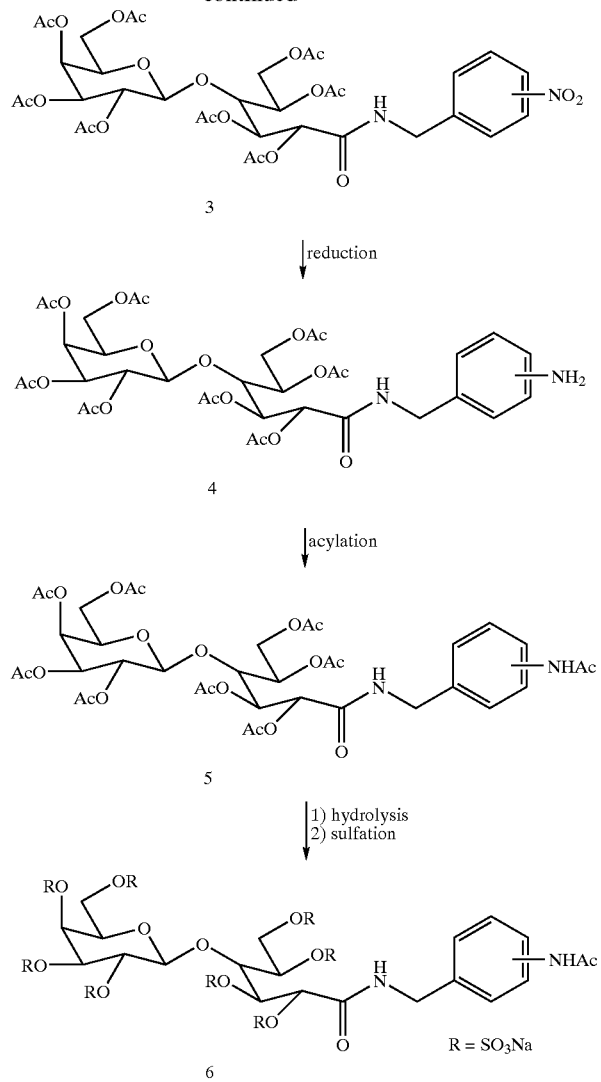

The compounds of this invention are useful as antiproliferative agents. The following procedures show the evaluation of representative compounds of this invention in standard pharmacological test procedure which measured ability of the evaluated compound to inhibit smooth muscle cell proliferation.

Effects of Compounds on Cell Proliferation Using $^3$H Thymidine Incorporation

Human and porcine smooth muscle cells were tested in early passage (generally passage 3–7) at sub-confluent conditions. Cultures were grown in 16 mm (24 well) multi-well culture dishes in medium 199 supplemented with 10% fetal bovine serum and 2% antibiotic/antimycotic. At sub-confluence, the cells were placed in a defined serum free medium (AIM-V; Gibco) for 24–48 h prior to initiating the experimental protocol.

Although compounds were found to be more effective with longer pre-incubations, in general, the procedures were initiated with the addition of compound, $^3$H thymidine and serum/growth factor to serum deprived synchronized cells and results are reported accordingly.

Compounds were added to each well at 50 fold dilution (20 μL/well) and the plates were incubated for 24–36 h at 37° C. in 5% $CO_2$. Compounds were initially dissolved in 50% ethanol and serially diluted into media. Compounds were routinely evaluated at concentrations from 1 to 100 μM. As a control, grade II porcine intestinal mucosal heparin (sodium salt) was routinely evaluated in all cell preparations at concentrations from 0.1 to 100 μg/mL.

At the completion of the test procedure, plates were placed on ice, washed three times with ice cold phosphate buffered saline (PBS) and incubated in ice cold 10% trichloroacetic acid (TCA) got 30 min to remove acid soluble proteins. Solution was transferred to scintillation vials containing 0.4 N HCl (500 μL/vial to neutralize NaOH) and each well was rinsed two times with water (500 μL) for a total volume of 2 mL/vial.

Data was obtained, in triplicate, for both control and experimental samples. Control (100%) data was obtained from maximally stimulated cells, as the result of growth factor or serum stimulation. Experimental data was obtained from cells maximally stimulated with growth factor or serum and treated with compound. Data are expressed as an $IC_{50}$ or percent inhibition in Table I below.

TABLE 1

| Compound of Example | Porcine Smooth Muscle Cell Antiproliferation IC50 |
| --- | --- |
| 1 | 118 μM |
| 2 | 45% @ 500 μM |
| 4 | 30% @ 500 μM |
| 5 | 12% @ 500 μM |
| 7 | 122 μM |

The compounds of this invention are useful in treating or inhibiting diseases which are characterized by excessive smooth muscle cell proliferation (smooth muscle cell hyperproliferation). The compounds are particularly useful in treating hyperproliferative vascular diseases which are characterized by smooth muscle cell hyperproliferation, such as restenosis, which most frequently arises from vascular reconstructive surgery and transplantation, for example, balloon angioplasty, vascular graft surgery, coronary artery bypass surgery, and heart transplantation. Other disease states in which there is unwanted "cellular" vascular proliferation include hypertension, asthma, and congestive heart failure. The compounds of this invention are also useful as inhibitors of angiogenesis. Angiogenesis (neovascularization), the process by which new capillaries are formed, is of principal importance for a number of pathological events including chronic inflammation and malignant processes. The compounds of this invention are therefore useful as antineoplastic agents.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, lethicins, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compounds of this invention can also be administered orally either in liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage requirements vary with the particular compositions employed, the route of administration, the severity of the symptoms presented and the particular subject being treated. Based on the results obtained in the standard pharmacological test procedures, projected daily dosages of active compound would be 0.1 to 10 mg/kg administered parenterally (intravenous preferred), with projected daily oral dosage being approximately ten-fold higher. Anticipated intravenous administration would last for approximately 5–30 days following acute vascular injury (i.e., balloon angioplasty or transplantation) and for a longer duration for the treatment of chronic disorders. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packaged powders, vials, ampoules, pre filled syringes or sachets containing liquids. The unit dosage form can be, for example, a capsule or tablet itself, or it can be the appropriate number of any such compositions in package form.

The following provides the preparation of representative compounds of this invention.

EXAMPLE 1

N-Benzyl-octa-O-acetyl-lactobionamide

Step 1

To a stirred solution of lactobiono-1,5-lactone (0.480 g, 1.41 mmol, *H. S. Isbell; H. L. Frush. Methods Carbohyd. Chem. 1963, 2, 16–18.) in warm MeOH (5 mL), from gentle heating, was added benzyl amine (0.177 mL, 1.62 mmol) dropwise. The reaction was stirred at rt for 18 h. After concentration, the oily residue was purified by recrystallization from i-PrOH to afford the product (0.300 g, 48%) as a glassy white solid; $^1$H NMR (DMSO-$d_6$) δ3.26–3.36 (m, 2H), 3.36–3.41 (m, 1H), 3.46–3.55 (m, 3H), 3.55–3.64 (m, 2H), 3.66–3.74 (m, 2H), 4.02–4.07 (m, 1H), 4.12 (d, J=5.9 Hz, 1H), 4.17 (dd, J=1.5, 5.1 Hz, 1H), 4.26 (d, J=7.0 Hz, 1H), 4.30 (d, J=6.4 Hz, 2H), 4.46–4.52 (m, 2H), 4.66 (t, J=5.7 Hz, 1H), 4.78 (dd, J=5.5, 9.7 Hz, 2H), 5.14 (d, J=3.7 Hz, 1H), 5.25 (d, J=5.7 Hz, 1H), 7.16–7.24 (m, 1H), 7.24–7.32 (m, 4H), 8.13 (t, J=6.2 Hz, 1H); IR (KBr) 3380, 2930, 2890, 1650, 1555, 1455, 1430, 1400, 1370, 1325, 1280, 1220, 1125, 1080, 1045, 970, 880, and 710 cm$^{-1}$; mass spectrum [(–) FAB], m/z 446 (M–H); Anal. Calcd. for $C_{19}H_{29}NO_{11}$: C, 51.00; H, 6.53; N, 3.13, Found: C, 50.87; H, 6.49; N, 3.12.

Step 2

To a stirred solution of N-benzyl-lactobionamide (0.150 g, 0.335 mmol) and triethylamine (0.822 mL, 5.90 mmol) in DMF (3.4 mL) at rt was added dropwise acetic anhydride (0.278 mL, 2.95 mmol) followed by a catalytic amount of DMAP (0.0327 g, 0.268 mmol). After 18 h, the mixture was concentrated, and the resulting residue was diluted with EtOAc (100 mL). This layer was washed with 1 N HCl (10 mL), sat. aq. NaHCO$_3$ (10 mL), and brine (10 mL) and then dried (MgSO$_4$). After concentration, the residue was purified by flash chromatography (10:90 to 90:10 EtOAc:petroleum ether gradient) to afford the product (0.221 g, 84%) as a glassy solid, mp 85–86° C.; $^1$H NMR (CDCl$_3$) δ1.88 (s, 3H), 1.90 (s, 3H), 1.98 (s, 3H), 2.02 (s, 6H), 2.03 (s, 3H), 2.09 (s, 3H), 2.15 (s, 3H), 3.94–4.02 (m, 2H), 4.03 (d, J=7.2 Hz, 1H), 4.11–4.19 (m, 2H), 4.23 (t, J=20.4 Hz, 1H), 4.27–4.37 (m, 2H), 4.79 (d, J=7.9 Hz, 1H), 4.84–4.95 (m, 2H), 5.14 (dd, J=3.7, 10.1 Hz, 1H), 5.21–5.24 (m, 1H), 5.45 (dd, J=3.1, 6.4 Hz, 1H), 7.17–7.25 (m, 3H), 7.26–7.32 (m, 2H), 8.58 (t, J=1.9 Hz, 1H); IR (KBr) 3390, 2970, 1755, 1670, 1540, 1420, 1375, 1220, 1130, 1050, 950, and 610 cm$^{-1}$; mass spectrum [(+) FAB], m/z 784 (M+H)$^+$, 806 (M+Na)$^+$; Anal. Calcd. for $C_{35}H_{45}NO19$: C, 53.64; H, 5.79; N, 1.79. Found: C, 53.51; H, 5.86; N, 1.82.

EXAMPLE 2

N-Benzyl-octa-O-sulfo-lactobionamide octasodium salt

To a stirred solution of N-benzyl-lactobionamide (0.760 g, 1.70 mmol) in DMF (59.4 mL) at rt was added sulfur trioxide trimethylamine complex (9.46 g, 68.0 mmol); this mixture was then heated to 70° C. After 4 days, the mixture was cooled to 0° C. and quenched with H$_2$O (60 mL). At this point, the solution was concentrated using no heat, and the resulting residue was slurried in H$_2$O (~20–25 mL) and filtered. The filtrate was applied to a G-10 Sephedex column. The resulting compound was collected and applied directly to a Dowex Na$^+$ ion exchange column to afford the product (1.47 g, 68%), after elution, as a glassy solid, mp >200° C. (decomp.); $^1$H NMR (D$_2$O) δ3.86 (t, J=6.2 Hz, 1H), 3.98–4.14 (m, 3H), 4.19–4.47 (m, 5H), 4.52–4.57 (m, 1H), 4.67–4.86 (m, 3H), 4.92–4.96 (m, 2H), 7.10–7.18 (m, 1H), 7.19–7.29 (m, 4H); IR (KBr) 3490, 2950, 2320, 1680, 1570, 1500, 1450, 1270, 1190, 1070, 1025, 920, 820, 700, 620, and 580 cm$^{-1}$; mass spectrum [(–) ESI], (m–zNa)/z 608.9 (M–2Na)$^{2-}$, 398.3 (M–3Na)$^{3-}$; Anal. Calcd. for $C_{19}H_{21}NO_{35}S_8Na_8\cdot3H_2O$: C, 17.32; H, 2.07; N, 1.06. Found: C, 17.12; H, 2.08; N, 1.03.

EXAMPLE 3

N-(4-Nitro-benzyl)-octa-O-acetyl-lactobionamide

To a stirred solution of lactobiono-1,5-lactone (5.00 g, 14.7 mmol, *H. S. Isbell; H. L. Frush. Methods Carbohyd. Chem. 1963, 2, 16–18.) in warm MeOH (53 mL), from gentle heating, was added 3-nitro-benzyl amine HCl salt (3.56 g, 19.1 mmol). The reaction was cooled to 0° C., followed by Na$_2$CO$_3$ (1.56 g, 14.7 mmol) addition, and then stirred at rt for 4 days. After concentration, the oily residue was taken up in DMF (74 mL). To this stirred solution at rt was added dropwise triethylamine (40.6 mL, 292 mmol) followed by acetic anhydride (13.7 mL, 146 mmol) and finally a catalytic amount of DMAP (1.63 g, 13.4 mmol). After 2 h, the mixture was concentrated, and the resulting residue was diluted with EtOAc (500 mL). This layer was washed with 1 N HCl (50 mL), sat. aq. NaHCO$_3$ (50 mL), and brine (50 mL) and then dried (MgSO$_4$). After concentration, the residue was purified by flash chromatography (0% to 40% acetone:CHCl$_3$ gradient) to afford the product (7.23 g, 59%) as a white foam, mp 100–103° C.; $^1$H NMR (CDCl$_3$) δ1.98 (s, 3H), 2.03 (s, 3H), 2.04 (s, 3H), 2.05 (s, 3H), 2.08 (s, 6H), 2.16 (s, 3H), 2.18 (s, 3H), 3.91 (t, J=7.0 Hz, 1H), 4.01 (dd, J=5.7, 12.5 Hz, 1H), 4.07 (dd, J=7.0, 11.2 Hz, 1H), 4.18 (dd, J=6.4, 11.2 Hz, 1H), 4.31 (dd, J=4.0, 6.6 Hz, 1H), 4.47 (dd, J=5.5, 15.8 Hz, 1H), 4.54 (dd, J=2.9, 12.5 Hz, 1H), 4.63 (d, J=7.9 Hz, 1H), 4.64 (dd, J=6.8, 15.8 Hz, 1H), 5.00 (dd, J=3.3, 10.3 Hz, 1H), 5.09 (td, J=2.9, 5.7 Hz, 1H), 5.17 (dd, J=7.9, 10.3 Hz, 1H), 5.38 (dd, J=1.1, 3.5 Hz, 1H), 5.59 (dd, J=4.0, 5.7 Hz, 1H), 5.63 (d, J=5.7 Hz, 1H), 6.66 (t, J=6.2 Hz, 1H), 7.41 (d, J=8.8 Hz, 2H), 8.16–8.21 (m, 2H); IR (KBr) 3400, 2980, 1755, 1670, 1560, 1525, 1420, 1380, 1360, 1220, 1125, 1050, 950, 900, 860, and 600 cm$^{-1}$; mass spectrum [(–) FAB], m/z 828 (M)$^-$; Anal. Calcd. for $C_{35}H_{44}N_2O_{21}\cdot0.5H_2O$: C, 50.18; H, 5.41; N, 3.34. Found: C, 50.21; H, 5.36; N, 3.29.

EXAMPLE 4

N-(4-Amino-benzyl)-octa-O-acetyl-lactobionamide

A solution containing N-(4-nitro-benzyl)-octa-O-acetyl-lactobionamide (6.97 g, 8.41 mmol) and tin (II) chloride dihydrate (13.3 g, 58.9 mmol) in EtOAc (167 mL) was refluxed for 4 h. The reaction was cooled to rt, carefully quenched with sat. aq. NaHCO$_3$ (until basic), diluted with EtOAc (163 mL), stirred for 0.5 h and filtered. The biphasic filtrate was separated and the aqueous phase extracted with EtOAc. The combined organic extracts were dried (Na$_2$SO$_4$) and concentrated. Purification by flash chromatography (0 to 30% methanol/CHCl$_3$ gradient) gave 4.61 g (69%) of the product as a glassy white solid, mp 87–91° C.; $^1$H NMR (CDCl$_3$) δ1.97 (s, 3H), 2.01 (s, 3H), 2.04 (s, 3H), 2.05 (s, 3H), 2.07 (s, 3H), 2.09 (s, 3H), 2.12 (s, 3H), 2.15 (s, 3H), 3.70 (s, 2H), 3.75 (td, J=0.9, 6.6 Hz, 1H), 4.00–4.17 (m, 3H), 4.25–4.38 (m, 3H), 4.50 (dd, J=2.9, 12.3 Hz, 1H), 4.59 (d, J=7.9 Hz, 1H), 4.95 (dd, J=3.5, 10.3 Hz, 1H), 5.03–5.07 (m, 1H), 5.17 (dd, J=7.9, 10.5 Hz, 1H), 5.33 (dd, J=1.1, 3.5 Hz, 1H), 5.58 (dd, J=3.1, 6.6 Hz, 1H), 5.61 (d, J=6.8 Hz, 1H), 6.38 (t, J=5.7 Hz, 1H), 6.62–6.67 (m, 2H), 7.02–7.07 (m, 2H); IR (KBr) 3390, 2980, 1745, 1670, 1630, 1530, 1425, 1375, 1220, 1125, 1060, 950, 900, 840, 755, and 620 cm$^{-1}$; mass spectrum [(+) FAB], m/z 799 (M+H)$^+$, 821 (M+Na)$^+$; Anal. Calcd. for $C_{35}H_{46}N_2O_{19}$·2.5H$_2$O: C, 49.82; H, 6.09; N, 3.32. Found: C, 49.84; H, 5.43; N, 3.33.

EXAMPLE 5

N-(3-Amino-benzyl)-octa-O-acetyl-lactobionamide

The title compound was prepared as a glassy foam (5.90 g, 63%) from N-(3-nitro-benzyl)-octa-O-acetyl-lactobionamide using a procedure similar to Example 4, mp 90–93° C.; $^1$H NMR (CDCl$_3$) δ1.97 (s, 3H), 2.01 (s, 3H), 2.04 (s, 3H), 2.05 (s, 3H), 2.07 (s, 3H), 2.09 (s, 3H), 2.14 (s, 3H), 2.15 (s, 3H), 3.76–3.83 (m, 3H), 4.03–4.18 (m, 4H), 4.29–4.41 (m, 2H), 4.50 (dd, J=2.9, 12.3 Hz, 1H), 4.60 (d, J=7.9 Hz, 1H), 4.97 (d, J=3.5, 10.5 Hz, 1H), 5.03–5.08 (m, 1H), 5.17 (dd, J=7.9, 10.5 Hz, 1H), 5.34 (dd, J=0.9, 3.3 Hz, 1H), 5.59 (dd, J=3.3, 6.6 Hz, 1H), 5.65 (d, J=6.6 Hz, 1H), 6.45 (t, J=5.9 Hz, 1H), 6.55–6.62 (m, 3H), 7.09 (t, J=7.9 Hz, 1H); IR (KBr) 3460, 3390, 2980, 1745, 1670, 1630, 1610, 1530, 1500, 1465, 1435, 1375, 25 1225, 1170, 1130, 1055, 955, 750, 700, 630, and 610 cm$^{-1}$; mass spectrum [(+) FAB], m/z 799 (M+H)$^+$, 821 (M+Na)$^+$; Anal. Calcd. for $C_{35}H_{46}N_2O_{19}$·1H$_2$O: C, 51.47; H, 5.92; N, 3.43. Found: C, 51.40; H, 5.70; N, 3.25.

EXAMPLE 6

N-[3-(Acetylamino)-benzyl]-octa-O-acetyl-lactobionamide

To a stirred solution of N-(3-amino-benzyl)-octa-O-acetyl-lactobionamide (2.90 g, 3.63 mmol) and triethylamine (1.11 mL, 7.99 mmol) in THF (45 mL) at 0° C. was added dropwise acetyl chloride (0.310 mL, 4.36 mmol). After 0.5 h at this temperature, it was warmed to rt and stirred an additional 72 h. At this point, the reaction was concentrated and taken up in EtOAc (300 mL). This organic solution was washed with 1 N HCl (30 mL), sat. aq. NaHCO$_3$ (30 mL), and brine (30 mL) and then dried (MgSO$_4$). After concentration, the residue was purified by flash chromatography (5% to 60% acetone:CHCl$_3$ gradient) to afford the product (2.35 g, 77%) as a glassy white foam, mp 120–123° C.; $^1$H NMR (CDCl$_3$) δ1.98 (s, 3H), 2.00 (s, 3H), 2.05 (s, 3H), 2.06 (s, 3H), 2.075 (s, 3H), 2.082 (s, 3H), 2.14 (s, 3H), 2.15 (s, 3H), 2.17 (s, 3H), 3.84–3.90 (m, 1H), 4.00–4.08 (m, 2H), 4.21 (dd, J=6.4, 11.2 Hz, 1H), 4.30 (dd, J=3.3, 6.8 Hz, 1H), 4.35 (dd, J=5.9, 14.9 Hz, 1H), 4.46–4.53 (m, 2H), 4.62 (d, J=7.9 Hz, 1H), 4.98 (dd, J=3.3, 10.3 Hz, 1H), 5.05 (td, J=2.9, 5.7 Hz, 1H), 5.19 (dd, J=7.9, 10.3 Hz, 1H), 5.36 (dd, J=1.1, 3.5 Hz, 1H), 5.56 (dd, J=3.1, 6.8 Hz, 1H), 5.69 (d, J=6.8 Hz, 1H), 6.64 (t, J=5.9 Hz, 1H), 6.96 (d, J=7.7 Hz, 1H), 7.21–7.30 (m, 2H), 7.66 (dd, J=1.1, 8.1 Hz, 1H), 7.81 (s, 1H); IR (KBr) 3390, 2990, 1755, 1675, 1620, 1560, 1490, 1425, 1375, 1220, 1130, 1055, 950, 755, and 610 cm$^{-1}$; mass spectrum [(+) FAB], m/z 841 (M+H)$^+$, 863 (M+Na)$^+$; Anal. Calcd. for $C_{37}H_{48}N_2O_{20}$·3H$_2$O C, 49.66; H, 6.08; N, 3.13. Found: C, 49.46; H, 5.37; N, 3.04.

EXAMPLE 7

N-[3-(Acetylamino)-benzyl]-octa-O-sulfo-lactobionamide octasodium salt

Step 1

A solution containing N-[3-(acetylamino)-benzyl]-octa-O-acetyl-lactobionamide (2.09 g, 2.49 mmol) and 25 weight % NaOMe in MeOH (42.6 μL, 0.746 mmol) in MeOH (62.7 ml) was refluxed for 2 h. The reaction was cooled to room temperature and concentrated, and the resulting residue was triturated with MeOH:Et$_2$O (30:70) to afford the product (1.11 g, 88%) as a glassy white solid, mp >170° C. (decomp.); $^1$H NMR (DMSO-d$_6$) δ2.01 (s, 3H), 3.16 (d, J=4.4 Hz, 2H), 3.31–3.42 (m, 1H), 3.47–3.63 (m, 4H), 3.68–3.73 (m, 2H), 4.01–4.14 (m, 3H), 4.14–4.33 (m, 4H), 4.44–4.53 (m, 2H), 4.63–4.70 (m, 1H), 4.73–4.87 (m, 2H), 5.12–5.19 (bs, 1H), 5.19–5.25 (bs, 1H), 6.95 (d, J=7.7 Hz, 1H), 7.19 (t, J=7.7 Hz, 1H), 7.38 (s, 1H), 7.48 (d, J=8.1 Hz, 1H), 8.09 (t, J=6.2 Hz, 1H), 9.86 (s, 1H); IR (KBr) 3380, 2920, 2320, 1660, 1620, 1600, 1560, 1495, 1430, 1370, 1320, 1275, 1080, 1050, 880, 780, and 700 cm$^{-1}$; mass spectrum [(+) FAB], m/z 527 (M+Na)$^+$; Anal. Calcd. for $C_{21}H_{32}N_2O_{12}$·1.5H$_2$O: C, 47.45; H, 6.64; N, 5.27. Found: C, 47.86; H, 6.73; N, 4.95.

Step 2

The title compound was prepared as a tan solid (1.76 g, 66%) from N-[3-(acetylamino)-benzyl]-lactobionamide using a procedure similar to Example 2, mp >211° C. (decomp.); $^1$H NMR (D$_2$O) δ1.98–2.01 (m, 3H), 3.74–3.92 (m, 1H), 3.98–4.17 (m, 3H), 4.20–4.56 (m, 6H), 4.66–4.85 (m, 3H), 4.87–4.98 (m, 2H), 6.96–7.08 (m, 2H), 7.18–7.27 (m, 1H), 7.30–7.36 (m, 1); IR (KBr) 3440, 2950, 1640, 1565, 1495, 1430, 1250, 1125, 1060, 1020, 920, 820, 695, 620, and 580 cm$^{-1}$; mass spectrum [(−) ESI], m/z 1297 (M−Na)$^-$, 1195 (M−SO$_3$Na+H−Na)$^-$, (m−zNa)/z 637.4 (M−2Na)$^{2-}$; Anal. Calcd. for $C_{19}H_{24}N_2O_{36}S_8Na_8$·6H$_2$O: C, 17.65; H, 2.54; N, 1.96. Found: C, 17.31; H, 2.13; N, 1.87.

What is claimed is:

1. A compound of formula I having the structure

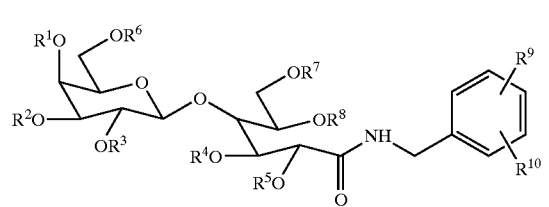

I wherein $R^1$, $R^2$, $R^3$, $R^4$, $R^5$, $R^6$, $R^7$, and $R^8$ are each, independently, acyl of 2–7 carbon atoms, haloacyl of 2–7 carbon atoms, nitroacyl of 2–7 carbon atoms, cyanoacyl of 2–7 carbon atoms, trifluoromethylacyl of 3–8 carbon atoms, or —SO$_3$H;

$R^9$ is hydrogen, CN, NO$_2$, halo, CF$_3$, alkyl of 1–6 carbon atoms, or alkoxy of 1–6 carbon atoms;

$R^{10}$ is hydrogen, —NO$_2$, —NHR$^{11}$, —NHR$^{13}$, —N(R$^{13}$)$_2$, —NCH$_3$R$^{13}$, —NHCO$_2$alkyl, wherein the alkyl moiety contains 1–6 carbon atoms, alkylsulfonamide of 1 to 4 carbon atoms,

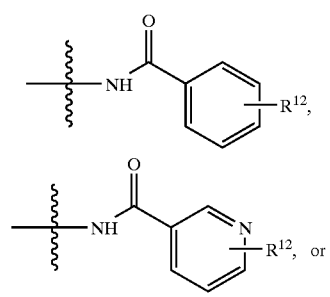

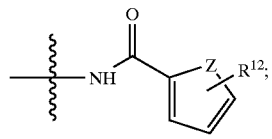

Z is O or S;

R[11] is an α-amino acid in which the α carboxyl group forms an amide with the nitrogen of R[10], wherein if said amino acid is glutamic acid or aspartic acid, the non-α carboxylic acid is an alkyl ester in which the alkyl moiety contains from 1–6 carbon atoms;

R[12] is hydrogen, CN, NO$_2$, halo, CF$_3$, alkyl of 1–6 carbon atoms, alkoxy of 1–6 carbon atoms, or acyl of 2–7 carbon atoms;

R[13] is hydrogen, acyl of 2–7 carbon atoms, haloacyl of 2–7 carbon atoms, nitroacyl of 2–7 carbon atoms, cyanoacyl of 2–7 carbon atoms, or trifluoromethylacyl of 3–8 carbon atoms;

or a pharmaceutically acceptable salt thereof.

2. The compound according to claim 1, wherein

R[1], R[2], R[3], R[4], R[5], R[6], R[7], and R[8] are each, independently, acyl of 2–7 carbon atoms or —SO$_3$H;

Z is O;

or a pharmaceutically acceptable salt thereof.

3. The compound according to claim 2, wherein

R[1], R[2], R[3], R[4], R[5], R[6], R[7], and R[8] are each, independently, acetyl or —SO$_3$H;

R[10] is hydrogen, —NO$_2$, —NHR[13], —N(R[13])$_2$,

R[13] is hydrogen, or acyl of 2–7 carbon atoms;

or a pharmaceutically acceptable salt thereof.

4. The compound of claim 1 which is:

a) N-Benzyl-octa-O-acetyl-lactobionamide or a pharmaceutically acceptable salt thereof;
b) N-Benzyl-octa-O-sulfo-lactobionamide or a pharmaceutically acceptable salt thereof;
c) N-(4-Nitro-benzyl)-octa-O-acetyl-lactobionamide or a pharmaceutically acceptable salt thereof;
d) N-(4-Amino-benzyl)-octa-O-acetyl-lactobionamide or a pharmaceutically acceptable salt thereof;
e) N-(3-Amino-benzyl)-octa-O-acetyl-lactobionamide or a pharmaceutically acceptable salt thereof;
f) N-[3-(Acetylamino)-benzyl]-octa-O-acetyl-lactobionamide or a pharmaceutically acceptable salt thereof; or
g) N-[3-(Acetylamino)-benzyl]-octa-O-sulfo-lactobionamide or a pharmaceutically acceptable salt thereof.

5. A pharmaceutical composition which comprises a compound of formula I having the structure

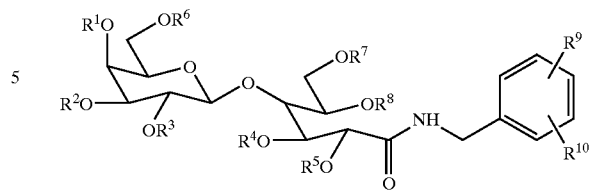

wherein

R[1], R[2], R[3], R[4], R[5], R[6], R[7], and R[8] are each, independently, acyl of 2–7 carbon atoms, haloacyl of 2–7 carbon atoms, nitroacyl of 2–7 carbon atoms, cyanoacyl of 2–7 carbon atoms, trifluoromethylacyl of 3–8 carbon atoms, or —SO$_3$H;

R[9] is hydrogen, CN, NO$_2$, halo, CF$_3$, alkyl of 1–6 carbon atoms, or alkoxy of 1–6 carbon atoms;

R[10] is hydrogen, —NO$_2$, —NHR[11], —NHR[13], —N(R[13])$_2$, —NCH$_3$R[13], —NHCO$_2$alkyl, wherein the alkyl moiety contains 1–6 carbon atoms, alkylsulfonamide of 1 to 4 carbon atoms,

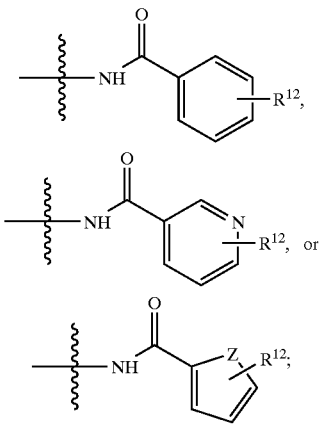

Z is O or S;

R[11] is an α-amino acid in which the α carboxyl group forms an amide with the nitrogen of R[10], wherein if said amino acid is glutamic acid or aspartic acid, the non-α carboxylic acid is an alkyl ester in which the alkyl moiety contains from 1–6 carbon atoms;

R[12] is hydrogen, CN, NO$_2$, halo, CF$_3$, alkyl of 1–6 carbon atoms, alkoxy of 1–6 carbon atoms, or acyl of 2–7 carbon atoms;

R[13] is hydrogen, acyl of 2–7 carbon atoms, haloacyl of 2–7 carbon atoms, nitroacyl of 2–7 carbon atoms, cyanoacyl of 2–7 carbon atoms, or trifluoromethylacyl of 3–8 carbon atoms;

or a pharmaceutically acceptable salt thereof, and a pharmaceutical carrier.

* * * * *